United States Patent [19]
Ruminson

[11] Patent Number: 4,704,125
[45] Date of Patent: Nov. 3, 1987

[54] INTRAOCULAR LENS FOR POSTERIOR CHAMBER IMPLANTATION

[76] Inventor: Wallace E. Ruminson, 444 W. Putnam, Porterville, Calif. 93257

[21] Appl. No.: 762,423

[22] Filed: Aug. 5, 1985

[51] Int. Cl.$^4$ .............................................. A61F 2/16
[52] U.S. Cl. ....................................................... 623/6
[58] Field of Search .......................................... 623/6

[56] References Cited

U.S. PATENT DOCUMENTS

| | | |
|---|---|---|
| 3,913,148 | 10/1975 | Potthast . |
| 4,134,161 | 1/1979 | Bayers . |
| 4,159,546 | 7/1979 | Shearing . |
| 4,177,526 | 12/1979 | Kuppinger et al. . |
| 4,190,049 | 2/1980 | Hager et al. . |
| 4,251,887 | 2/1981 | Anis . |
| 4,280,232 | 7/1981 | Hommel ............................. 623/6 |
| 4,343,050 | 8/1982 | Kelman . |
| 4,476,591 | 10/1984 | Arnott . |
| 4,585,454 | 4/1986 | Fabricant ............................. 623/6 |

Primary Examiner—Richard J. Apley
Assistant Examiner—James Prizant
Attorney, Agent, or Firm—Kelly, Bauersfeld & Lowry

[57] ABSTRACT

An intraocular lens of the type having a transparent lens body and a pair of oppositely projecting curved resilient support loops, wherein the lens is designed for facilitated implantation into the posterior chamber of the eye following extracapsular extraction of a natural lens. A first loop carries a guide blade projecting toward the lens body and including an aperture near said first loop for receiving a retention tab projecting posteriorly from the lens body periphery to retain the first loop compressed closely alongside the lens body periphery with a substantial portion of the blade lying along the posterior surface of the lens body. Upon lens implantation into the posterior chamber, for example, through a corneal incision and the pupil, the lens is oriented with the second loop in a leading position for easy seating within the capsular bag, while the first loop is retained by the tab until the lens is fully seated within the capsular bag. The guide blade is then released from the tab permitting the first loop to spring outwardly with the guide blade maintained posteriorly of the lens body through a substantial initial portion of this movement to insure seating within the capsular bag. A forceps instrument is also disclosed for handling the improved lens and for disengaging the guide blade from the retention tab during an implantation procedure.

19 Claims, 11 Drawing Figures

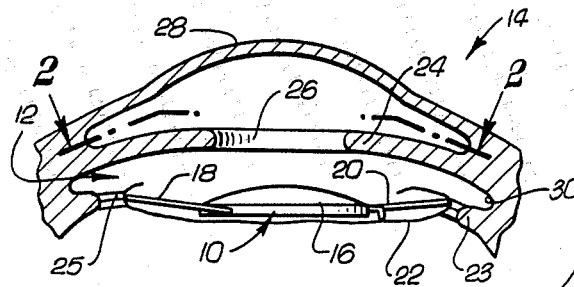
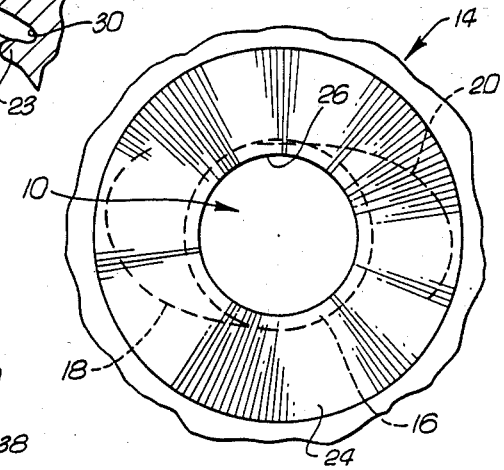
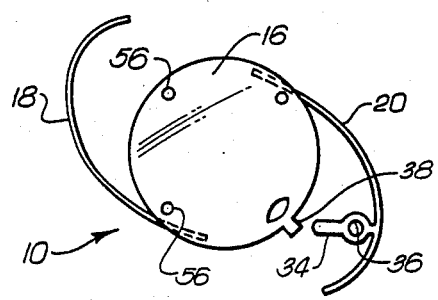
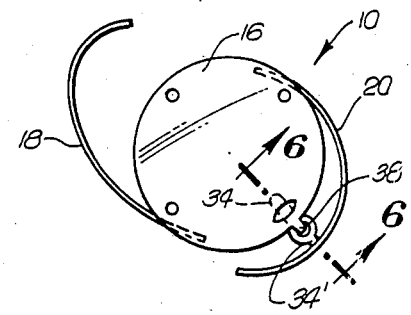
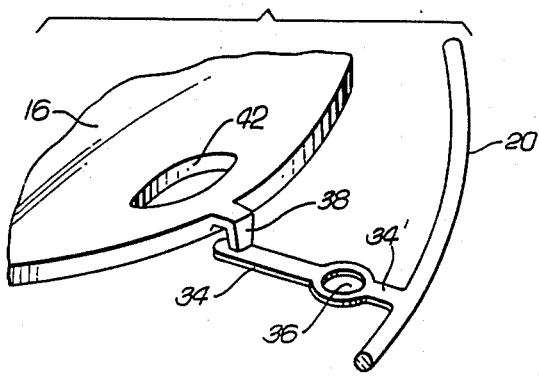
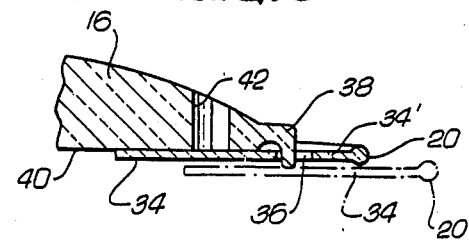

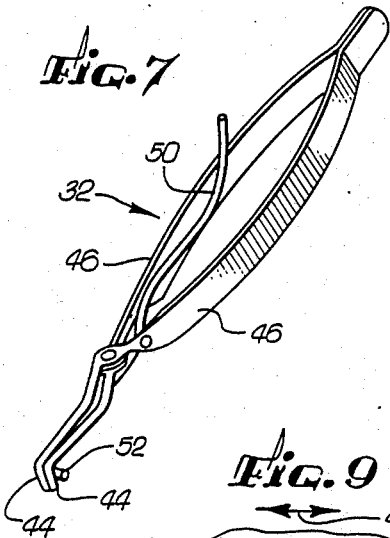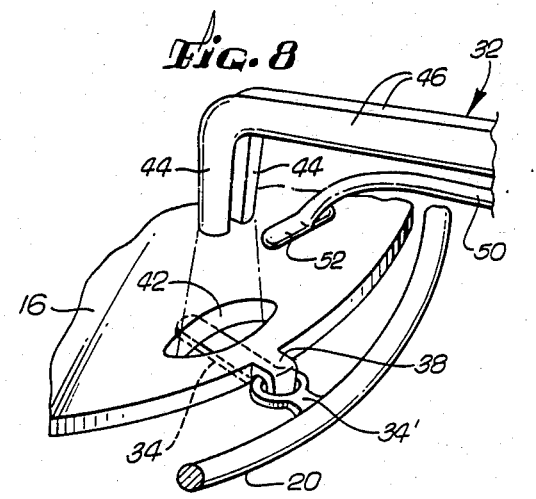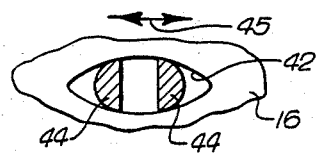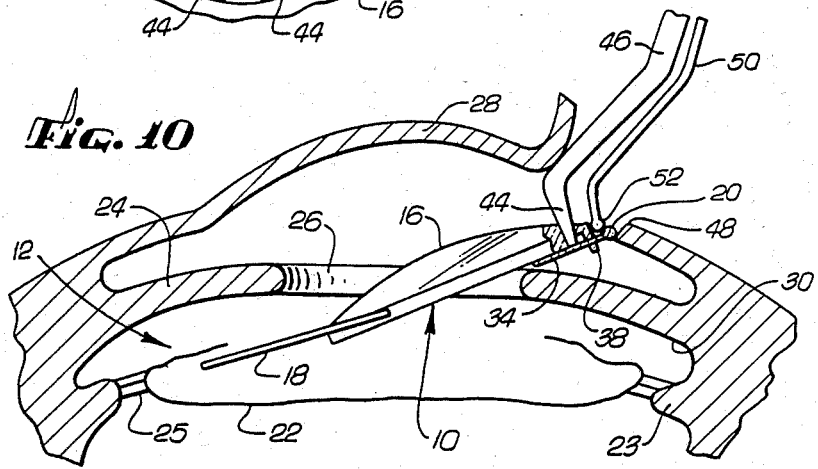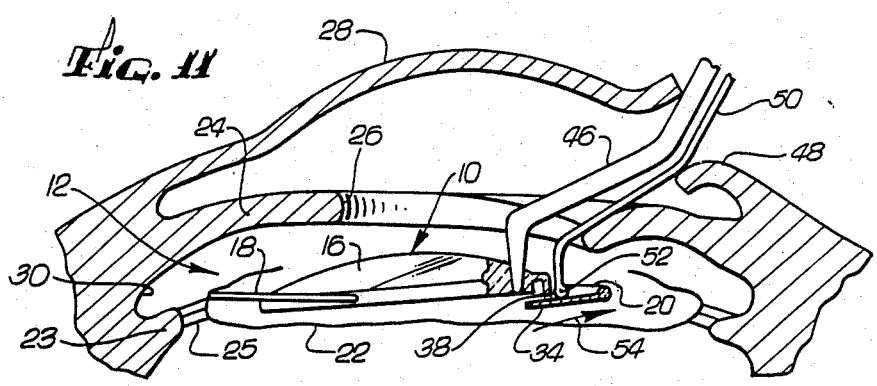

INTRAOCULAR LENS FOR POSTERIOR CHAMBER IMPLANTATION

BACKGROUND OF THE INVENTION

This invention relates generally to intraocular lenses designed for implantation into the eye as a replacement for a surgically removed natural lens. More specifically, this invention relates to an improved intraocular lens designed for posterior chamber implantation and including means for positive seating of resilient centering and fixation loops for the lens within the capsular bag in the posterior chamber of the eye.

Intraocular lenses in general are well known for implantation into the eye as a replacement for a natural crystalline lens which has been removed surgically due to a cataract condition, injury, or the like. Such intraocular lenses typically are constructed from a transparent lens body of a selected, relatively inert plastic material, such as polymethylmethacrylate, having a generally disk-shaped configuration providing optical characteristics approximating a natural lens. Resilient support loops are normally provided to project outwardly from the periphery of the lens body with a smooth, outwardly convex curvature for supporting and centering the lens body with respect to adjacent delicate eye tissue. In accordance with some intraocular lens configurations, the lens body and support loops are designed for seating in the so-called anterior chamber of the eye in front of the iris and pupil, whereas other lens designs are intended for implantation within the so-called posterior chamber behind the iris and pupil.

In accordance with recent trends in ophthalmic surgery, posterior chamber lens implantation is preferred by many surgeons largely because the lens prosthesis is positioned within the eye at or near the original position of the natural lens. More particularly, posterior chamber implantation of an intraocular lens commonly follows so-called extracapsular extraction wherein a central anterior wall region of a transparent capsular bag or membrane containing the natural lens is surgically removed to accomodate natural lens removal while leaving the remainder of the capsular bag intact. The intraocular lens implant is then inserted through the pupil margin into the posterior chamber desirably with the resilient support loops seated within the periphery of the capsular bag.

Implantation of an intraocular lens including the resilient support loops fully into the capsular bag, however, constitutes a relatively difficult surgical procedure. In particular, the lens implant is normally held in an angular orientation during insertion through a corneal incision and further through the pupil into the posterior chamber with one of the loops leading lens insertion and thus angled downwardly for relatively easy seating into the capsular bag, typically within the inferior margin thereof. However, significant lens manipulation is normally required to fit the trailing support loop through the pupilary margin and further to manipulate the trailing loop for seating within the capsular bag, as opposed to seating against the more sensitive ciliary sulcus region within the posterior chamber forwardly of the ciliary muscle and the capsular bag. Such manipulation normally requires sequential insertion into the eye of different surgical instruments thereby prolonging the surgical procedure and increasing risk of eye trauma, particularly to endothelial cells on the interior of the cornea. More- over, the superior margin of the capsular bag into which the trailing loop desirably fits is extremely difficult or impossible for the surgeon to see, whereby positive seating of the trailing loop into the capsular bag frequently cannot be assured.

There exists, therefore, a significant need for an improved intraocular lens designed for positive implantation into the capsular bag within the posterior chamber of the eye following extracapsular extraction, wherein the improved lens is implanted by use of a single surgical instrument inserted into the eye a single time. The present invention fulfills these need and provides further related advantages.

SUMMARY OF THE INVENTION

In accordance with the invention, an improved intraocular lens is provided for posterior chamber implantation with positive support loop seating within the capsular bag, if desired. Lens implantation is performed quickly and easily with one-time insertion of a single surgical instrument, thereby reducing manipulative and surgical steps and minimizing patient eye trauma.

The improved intraocular lens comprises a transparent lens body of a selected, relatively insert material such as polymethylmethacrylate and shaped to have a generally conventional optical geometry. The lens body carries an oppositely projecting pair of curve resilient support loops which may be formed integrally with the lens body or, in accordance with conventional practice, separately attached to the lens body during manufacture. These support loops extend from opposite points on the lens body periphery with a curved C-shaped or J-shaped geometry to provide smooth outwardly convex surfaces for centering and supporting the lens body relative to a pupillary sight line when the lens is implanted into the posterior chamber.

A first one of the loops carries an elongated loop guide blade projecting toward the lens body periphery from a position spaced from the distal end of said loop. An aperture is formed in the guide blade near the first loop, wherein said aperture is sized for reception of a relatively small retention tab projecting posteriorly from a predetermined position at the lens body periphery. Accordingly, prior to lens implantation, the first loop may be compressed radially inwardly to lie alongside the lens body periphery and with the retention tab projecting into the guide blade aperture. In this configuration, a substantial portion of the guide blade projects radially inwardly from the lens body periphery in sliding contact with a posterior surface of the lens body.

The intraocular lens is implanted into the posterior chamber by insertion, for example, through a corneal incision and further through the pupil with the other or second loop in a leading position relative to the lens body. During such implantation, the second loop is angled downwardly upon passage through the pupil for direct, relatively easy seating into the capsular bag, normally into the inferior margin of said bag, subsequent to extracapular extraction of a natural lens. The retention tab maintains the first loop closely against the lens body for relatively easy passage through the pupil thereby facilitating full insertion of the lens into the capsular bag. When such full insertion is achieved, the guide blade is depressed sufficiently for release from the retention tab whereupon the first loop resiliently springs outwardly from the lens body periphery. However, the first loop is maintained in a posterior attitude through a substantial initial portion of such outward movement, thereby insuring positive seating of the first loop into the capsular bag, typically within the superior margin thereof.

A surgical forceps includes a pair of tongs having relatively small grasping tips sized and shaped for relatively easy insertion into a generally oval-shaped pick-up opening formed near the lens body periphery at a position closely adjacent the retention tab. Light manual or spring pressure on the tongs urges the grasping tips to spread apart within the pick-up opening to securely grasp the lens body during surgical implantation into the posterior chamber. A release bar is pivotally carried by the forceps and movable upon lens insertion fully into the capsular bag to depress and release the guide blade from the retention tab thereby permitting the first support loop to spring outwardly while initially maintained posteriorly for seating into the periphery of the capsular bag.

Other features and advantages of the present invention will become more apparent from the following detailed description, taken conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a side elevation view illustrating an intraocular lens embodying the novel features of the invention and implanted within the capsular bag in the posterior chamber of an eye;

FIG. 2 is a fragmented sectional view taken generally on the line 2—2 of FIG. 1;

FIG. 3 is a top plan view of the improved intraocular lens embodying the invention and illustrating lens support loops in an expanded configuration;

FIG. 4 is a top plan view similar to FIG. 3 but illustrating one of the support loops in a compressed configuration;

FIG. 5 is an enlarged fragmented perspective view illustrating a portion of the lens;

FIG. 6 is an enlarged fragmented vertical section taken generally on the line 6—6 of FIG. 4;

FIG. 7 is a perspective view illustrating a surgical forceps instrument for use in implanting the improved lens;

FIG. 8 is an enlarged fragmented perspective view illustrating grasping of the lens with the surgical instrument of FIG. 7, with one of the lens support loops being shown in the compressed configuration;

FIG. 9 is an enlarged fragmented sectional view illustrating grasping engagement between the surgical instrument and the lens;

FIG. 10 is an enlarged side elevation view similar to FIG. 1 illustrating an initial step in posterior chamber implantation of the lens; and FIG. 11 is another enlarged side elevation view illustrating further steps in posterior chamber implantation of the lens.

DETAILED DESCRIPTION OF THE PREFERRED EMBODIMENT

As shown in the exemplary drawings, an improved intraocular lens referred to generally by the reference numeral 10 is provided for facilitated implantation into the posterior chamber 12 of an eye 14. The intraocular lens comprises a transparent lens body 16 supported and centered within the posterior chamber 12 by an oppositely projecting pair of resilient support loops 18 and 20, wherein the lens includes means for assuring positive seating thereof within the capsular bag 22 in the posterior chamber.

The improved intraocular lens 10 of the present invention is designed for implantation into the eye following surgical removal of the natural lens (not shown). More particularly, the natural crystalline lens or the eye is encapsulated within a transparent membrane referred to commonly as the capsular bag supported from the ciliary muscle 23 by suspensory ligaments or zonules 25 within a shallow chamber posteriorly of the iris 24 and the pupil opening 26 formed by the iris. Light passing through the transparent cornea 28 at the front of the eye passes further through the pupil 26 and is normally focused by the natural lens upon the retina (also not shown) at the rear of the eyeball. However, in the event the natural lens becomes clouded or otherwise experiences impaired transparency, for example, due to a cataract condition, injury, or the like, the natural lens can be removed surgically and replaced by an intraocular lens implant of the type corresponding with the invention.

In accordance with one technique preferred by many ophthalmic surgeons, such technique being commonly referred to as extracapsular extraction, the natural lens of the eye is surgically removed by accessing the anterior side of the capsular bag 22 through a corneal incision and further through the pupil 26. The anterior side of the capsular bag is removed leaving the bag peripheral margin and posterior wall intact. The natural lens is thus exposed for surgical removal, with one well known surgical removal technique comprising ultrasonic emulsification in combination with particulate aspiration. The intraocular lens implant is then implanted through the incision and the pupil to a position seated within the posterior chamber 12 and thus in a position closely corresponding with the natural lens prior to removal. The lens implant is conventionally centered and supported within the posterior chamber by two or more outwardly projecting haptics commonly in the form of curved resilient support loops which engage a peripheral region of the posterior chamber. For an example of a posterior chamber lens of this general type, see U.S. Pat. No. 4,159,546.

The improved intraocular lens 10 of the present invention is designed for relatively simple surgical implantation into the posterior chamber of the eye with the resilient support loops 18 and 20 positively seated within the capsular bag 22. The invention thus avoids undesired seating of the support loops against other tissue at the periphery of the posterior chamber 12, particularly such as one or both of the loops seating against the more sensitive ciliary sulcus region 30 disposed forwardly of the capsular bag 22 and the ciliary muscle 23. This positive seating of the lens support loops within the capsular bag is further faciliated by a unique forceps surgical instrument 32 (FIG. 7) designed for simplified implantation of the improved lens 10 in a single instrument insertion step. Accordingly, the invention eliminates use of additional lens manipulatory instruments and further decreases the time required for an implantation procedure, thereby minimizing risk of trauma to the eye.

As shown best in FIGS. 1–6, the transparent lens body 16 of the improved intraocular lens 10 has a generally conventional disk-shaped geometry with a convex anterior surface and planar posterior surface being shown in the drawings by way of example. The particular lens geometry is selected to provide a desired set of optical characteristics in accordance with the sight requirements of the individual patient. If desired, ridges or other spacing elements (not shown) may be included at the posterior side of the lens body to facilitate secondary capsulotomies using modern laser surgery techniques, all in a manner known to those skilled in the art.

The transparent lens body 16 is formed from a highly transparent, relatively inert and desirably lightweight material, with polymethylmethacrylate being used commonly throughout the intraocular lens industry. The support loops 18 and 20 are also formed from a relatively inert material such as polypropylene or the like selected to have substantial resiliency urging the loops with a springlike action in a radially outward direction spaced from the lens body periphery. In one common form, as depicted in the illustrative drawings, the loops have a generally C-shaped or J-shaped configuration projecting outwardly from generally opposed lateral points on the periphery of the lens body 16. As shown best in FIG. 3, these support loops 18 and 20 have inboard or proximal ends anchored in any suitable manner at opposite lateral positions on the lens body and protrude outwardly therefrom with mirror image curvature to define outwardly presented curved convex support surfaces. The distal ends of the support loops are spaced from the lens body periphery to accommodate radial inward compression of the loops toward the lens body in a resilient manner functioning when implanted to center and support the lens body within the capsular bag 22 in substantial alignment with the pupil 26. Moreover, as shown best in FIG. 1, these loops may be provided with an anterior component of angulation typically about 5-15 degrees to assist in maintaining the lens body 16 posteriorly of the pupil. Alternately, the loops 18 and/or 20 may be molded or otherwise formed integrally with the lens body 16, if desired.

In accordance with one primary aspect of the invention, a relatively thin and substantially flat guide blade 34 is carried by the support loop 20 in a generally midrange position along the length of the loop 20 to project generally radially toward the periphery of the lens body. This guide blade 34 is attached to the support loop 20 by any suitable attachment means, or, alternately, the guide blade 34 may be formed integrally therewith. The width of the guide blade 34 is widened at a position near its juncture with the loop 20 to accomodate a relatively small aperture 36. The size and shape of this aperture 36 is selected for reception of a small retention tab 38 formed at the periphery of the lens body 16 and projecting posteriorly a short distance therefrom. This tab 38 is preferably located substantially at the superior margin of the lens body 16 when implanted into the eye, as will be described in more detail.

Accordingly, prior to implantation of the improved intraocular lens 10, the support loop 20 can be compressed radially inwardly toward the periphery of the lens body 16 for reception of the retention tab 38 within the guide blade aperture 36, thereby locking the support loop 20 in a position lying closely alongside the lens body periphery, as shown best in FIG. 4. In this position, a substantial portion of the guide blade 34 projects radially inwardly beyond the lens body periphery and lies substantially flush against the posterior surface 40 of the lens body, as viewed in FIG. 6.

A generally oval-shaped and axially oriented pick-up opening 42 is formed in the lens body 16 at a position closely adjacent the retention tab 38. This pick-up opening 42 is sized and shaped for receiving a pair of relatively small grasping tips 44 formed respectively at the ends of a complementary-shaped pair of tongs 46 forming the surgical forceps instrument 32, as shown in FIGS. 7-9. More particularly, these grasping tips 44 each have a generally semicircular cross-sectional shape with convex surfaces presented laterally away from each other and sized for reception together into the larger central region of the pick-up opening 42. The tongs 46 are suitably pivoted and/or spring-loaded for relative movement of the grasping tips 44 normally into contact with each other. Alternatively, if desired, the tongs 46 may be spring-loaded for movement of the tips 44 toward spaced positions, wherein light manual pressure is required to move the tips into contact with each other.

In use, the grasping tips 44 of the instrument 32 are inserted easily into the lens body pick-up opening 42 whereupon the tips 44 are laterally separated as depicted by arrow 45 by light manual squeezing pressure applied to the tongs 46 with one hand. This displaces the grasping tips 44 into grasping engagement with the lens body 16 near the smaller opposed ends of the pick-up opening 42, as shown in FIG. 9. The lens 10 can then be lifted and manipulated with the surgical instrument 32 using a single hand.

As shown in FIGS. 10 and 11, the intraocular lens 10 can be implanted quickly and easily with a single insertion of the surgical instrument 32 into the eye. More specifically, the lens 10 is grasped with the instrument 32 and passed through a corneal incision 48 and further through the pupil 26 into the posterior chamber 12. During such insertion, the patient is normally prone whereby the lens is angularly oriented with a leading end angled downwardly toward the posterior chamber 12 and the capsular bag 22. Importantly, the forceps instrument 32 holds the lens 10 with the support loop 18 in a leading position angled sufficiently downward as viewed in FIG. 10 for relatively easy seating into the peripheral margin, normally the inferior margin of the capsular bag 22. In this regard, the tongs 46 are conveniently provided with appropriate contour for facilitated lens implantation through an incision 48 of minimum size and at a location displaced from a normal line of vision.

Continued lens insertion moves the remainder of the lens body 16 and the trailing support loop 20 through the pupil to a position substantially fully within the capsular bag, as shown in FIG. 11. In this position, a release bar 50 pivotally supported by one or both of the forceps tongs 46 is pivoted easily while holding the instrument 32 with one hand to move a foot 52 on the release bar downwardly against the portion 34' of the guide blade 34 between the aperture 36 and the support loop 20. This downward movement displaces the guide blade 34 in a posterior direction sufficiently for release from the retention tab 38, whereupon the resilient loop 20 displaces radially outwardly toward a normal unstressed position and further toward the periphery of the capsular bag 22, as illustrated by arrow 54 in FIG. 11. Importantly, throughout a substantial initial portion of this outward loop displacement, the guide blade 34 is maintained in a posterior attitude by the foot 52 and/or by contact with the posterior side 40 of the lens body 16 and/or the tab 38 to correspondingly maintain the loop 20 in a posterior position thereby assuring positive loop seating within a peripheral region of the capsular bag 22, typically at the superior margin thereof. Such positive loop seating is assured notwithstanding conventional forward angulation of the loops 18 and 20.

With the implantation procedure completed, the manual pressure applied to the tongs 46 is released sufficiently to release the grasping tips 44 from the lens body 16. The instrument 32 can then be withdrawn quickly and easily through the incision 48. The lens 10 is thus fully implanted with the loops 18 and 20 properly seated within the capsular bag, all without requiring use of additional surgical instruments or subsequent lens manipulatory steps which can increase risk of trauma to the eye and prolong the surgical procedure. However if additional manipulation is desired or necessary, conventional positioning holes 56 can be formed about the periphery of the lens body 16 for registry with manipulatory instruments, although their use will generally be unnecessary with the lens 10 of the invention.

A variety of further improvements and modifications to the invention described herein are believed to be apparent to those skilled in the art. Accordingly, no limitation on the invention is intended by way of the description herein, except as set forth as the appended claims.

What is claimed is:

1. An intraocular lens for implantation into the posterior chamber of the eye in a position seated within the capsular bag subsequent to extracapsular extraction of the natural lens, said intraocular lens comprising:
    a transparent lens body having a generally disk-shaped configuration;
    a plurality of resilient support loops projecting outwardly from the periphery of said lens body;
    an elongated guide blade carried by one of said loops to project from said one loop in a direction generally toward the periphery of said lens body, said guide blade having an aperture formed therein at a position generally near said one loop; and
    a retention tab projecting posteriorly a short distance from the periphery of said lens body;
    said one loop being movable to a compressed position relatively closely alongside the lens body periphery and retained thereat by reception of said tab into the guide blade aperture and with a substantial portion of said guide blade lying along a posterior surface of said lens body, said one loop being releasable from said compressed position upon posterior displacement of said guide blade relative to said tab whereupon said one loop moves resiliently in an outward direction with respect to the lens body periphery, said guide blade maintaining said one loop in a generally posterior attitude throughout at least a substantial initial portion of the resilient outward movement.

2. The intraocular lens of claim 1 wherein said plurality of support loops comprises a pair of support loops projecting outwardly from generally opposed positions at the periphery of said lens body.

3. The intraocular lens of claim 2 wherein each of said loops has an inboard end anchored to said lens body and an outboard end spaced from the periphery of said lens body.

4. The intraocular lens of claim 2 wherein each of said loops is curvedly configured to provide a relatively smoothly and outwardly convexly curved support surface.

5. The intraocular lens of claim 1 wherein said guide blade is relatively thin and generally planar.

6. The intraocular lens of claim 1 wherein said lens body has an inferior margin and a superior margin, said retention tab projecting posteriorly generally from said superior margin.

7. The intraocular lens of claim 1 wherein said lens body has a pick-up opening formed therein at a position generally adjacent said retention tab.

8. The intraocular lens of claim 7 wherein the pick-up opening in said lens body is generally oval-shaped.

9. The intracular lens of claim 7 further including a surgical instrument for use in implanting the lens into the eye, said instrument including grasping means for engaging said lens body within the pick-up opening to hold said lens body during implantation into the eye, and release means for displacing said guide blade posteriorly relatively to said tab to release said guide blade from said tab, said grasping means being releasable for withdrawal of said instrument from the eye leaving said lens body implanted within the eye.

10. The intraocular lens of claim 9 wherein said release means includes means for maintaining said guide blade in said posterior attitude throughout said initial portion of resilient outward movement.

11. The intraocular lens of claim 1 wherein said support loops are angulated anteriorly.

12. As intraocular lens for implantation into the eye, comprising:
    a lens body having a generally disk-shaped configuration;
    a plurality of resilient support loops projecting outwardly generally from the periphery of said lens body;
    means for releasably reataining at least one of said loops in a compressed position relatively closely alongside the periphery of said lens body during implantation into the eye, said retaining means being releasable within the eye to permit said at least one loop to move outwardly relative to the lens body periphery; and
    means for maintaining said at least one loop in a posterior attitude relative to said lens body throughout at least an initial portion of outward movement continuing substantially beyond the periphery of said lens body upon release of said retaining means, said maintaining means including a guide blade on said at least one loop and projecting therefrom generally toward the periphery of said lens body, said guide blade having a substantial portion thereof lying along a posterior surface of said lens body when said at least one loop is in the compressed position.

13. The intraocular lens of claim 12 wherein said plurality of support loops comprises a pair of support loops projecting outwardly from generally opposed positions at the periphery of said lens body.

14. The intraocular lens of claim 12 further including a surgical instrument for use in implanting the lens into the eye, said instrument including grasping means for holding said lens body during implantation into the eye, and release means for releasing said at least one loop from said compressed position, said release means operably cooperating with said at least one loop for maintaining said one loop in said posterior attitude throughout said initial portion of said outward movement continuing substantially beyond the periphery of said lens body, said grasping means being releasable for withdrawal of said instrument from the eye leaving said lens body within the eye.

15. An intraocular lens for implantation into the posterior chamber of the eye in a position seated within the capsular bag subsequent to extracapsular extraction of the natural lens, said intraocular lens comprising:
- a transparent lens body of generally disk-shaped configuration;
- leading and trailing resilient support loops having respective inboard ends anchored to the periphery of said lens body generally at opposite positions thereon and outboard ends spaced from the lens body periphery, said loops projecting outwardly from said lens body with an outwardly presented convexly curved configuration;
- an elongated and relatively thin guide blade projecting from said trailing loop near the outboard end thereof in a direction generally toward the lens body periphery, said guide blade having an aperture therein near said trailing loop; and
- a retention tab projecting posteriorly a short distance from the lens body periphery, said trailing loop being compressible to a position lying closely alongside the lens body periphery with said tab received into the guide blade aperture and with said guide blade lying along a posterior surface of said lens body, said guide blade being movable in a posterior direction for release from said tab whereupon said trailing loop displaces resiliently outwardly from the lens body periphery, said guide blade maintaining said trailing loop substantially in a posterior attitude throughout an initial portion of said outward movement.

16. The intraocular lens of claim 15 wherein said lens body has a pick-up opening formed therein at a position generally adjacent said retention tab.

17. The intraocular lens of claim 16 further including a surgical instrument for use in implanting the lens into the eye, said instrument including grasping means for engaging said lens body within the pick-up opening to hold said lens body during implantation into the eye, and release means for displacing said guide blade posteriorly relatively to said tab to release said guide blade from said tab, said release means maintaining said guide blade in said posterior attitude throughout said initial portion of said outward movement, said grasping means being releasable for withdrawal of said instrument from the eye leaving said lens body implanted within the eye.

18. The intraocular lens of claim 17 wherein said surgical instrument comprises a forceps having a pair of tongs, said grasping means comprises a pair of grasping tips on said tongs, and said release means comprises a release bar pivotally supported by at least one of said tongs and including a foot for displacing said guide blade posteriorly relative to said tab upon pivoting motion of said release bar relative to said at least one of said tongs.

19. The intraocular lens of claim 18 wherein said foot on said release bar is disposed for engaging said guide blade at a position generally between the aperture and said trailing loop.

* * * * *